United States Patent [19]

Laragh

[11] Patent Number: 5,399,581
[45] Date of Patent: Mar. 21, 1995

[54] METHOD AND COMPOSITIONS FOR TREATMENT OF SEXUAL IMPOTENCE

[76] Inventor: John H. Laragh, 435 E. 70th St., New York, N.Y. 10021

[21] Appl. No.: 633,753

[22] Filed: Dec. 26, 1990

[51] Int. Cl.$^6$ .................. A61K 31/415; A61K 31/40; A61K 31/17; A61K 31/165
[52] U.S. Cl. .................................. 514/396; 514/399; 514/411; 514/597; 514/620; 514/651
[58] Field of Search ............... 514/248, 396, 399, 411, 514/597, 620, 651

[56] References Cited

U.S. PATENT DOCUMENTS 4,801,587  1/1989  Voss et al. ................... 514/248
4,840,952  6/1989  Gamble et al. ................ 514/253

OTHER PUBLICATIONS

Gwinup, G., *Annals of Internal Medicine*, pp. 162–163 (Jul. 1988).

*Primary Examiner*—Raymond J. Henley, III
*Attorney, Agent, or Firm*—Patrea L. Pabst

[57] ABSTRACT

A method and compositions is described for treating sexual impotence with an oral drug regimen amenable to once a day therapy. The method combines the administration of a non-selective alpha$_1$-alpha$_2$ adrenergic blocking drug, such as dibenzyline, with that of a particular type of beta adrenergic blocking agent which also possesses vasodilator activity, such as labetalol, celiprolol, or carvedilol. The net effect is a reciprocally balanced autonomic blockade in which the reactive beta adrenergic activity induced by pure alpha blockade is blocked by the beta-blockade while the unopposed or reactive alpha adrenergic tone consequent to pure beta blocker therapy is blocked by the alpha blocker. Accordingly, while each drug given by itself, either the alpha adrenergic blocker or the vasodilating beta adrenergic blocker, produces no benefit or at times some small benefit, the combined therapy works for restoring or enabling sexual function.

11 Claims, No Drawings

METHOD AND COMPOSITIONS FOR TREATMENT OF SEXUAL IMPOTENCE

BACKGROUND OF THE INVENTION

This invention generally relates to pharmaceuticals and more specifically to a method and compositions for treating patients with sexual impotence.

Sexual impotence in males may be defined as a failure of penile erection accompanied at times by a failure of ejaculation and orgasm. The known causes for this disability are related to conditions involving failure of male hormone production and are rare. For the majority of cases no hormonal or primary structural defects are clinically demonstrable. Such instances have been considered by exclusion to be on a "vasculogenic" basis, or due to a failure or abnormality of neural control of the genital vasculature, possibly arising from central nervous system dysfunction and possibly involving psychogenic factors. This common type of impotence usually increases in frequency with advancing age.

Alpha-1 receptors have a number of functions in the sympathetic nervous system, including mediation of ejaculation. Located at the postsynaptic effector sites in smooth muscle and gland cells, stimulation of these alpha-1 receptors by norepinephrine causes an excitatory response. In arteries, such stimulation results in constriction of the blood vessels and an increase in blood pressure. Alpha-2 receptors, located at presynaptic effector sites in smooth muscle and gland cells, mediate feedback inhibition of neural release of norepinephrine. There are also post-synaptic extrajunctional alpha-2 receptors, located nearer to the vascular intima which transduce vasoconstriction in response to circulating epinephrine or norepinephrine. Stimulation of beta-1 receptors, located predominantely in the heart, causes an increase in heart rate and cardiac contractility. Beta-2 receptors, located primarily in smooth muscle and gland cells, evoke inhibitory responses when stimulated such as dilatation of arteries causing a decrease in blood pressure.

Knowledge of these receptors and their functions has been used to develop a number of pharmacological agents. Most notably, antihypertensive drugs, referred to as adrenergic blocking drugs, have been produced which block alpha-1 receptors and beta-1 receptors by blocking the effect of the neurotransmitters adrenaline (epinephrine) and noradrenaline (norepinephrine) in the sympathetic nervous system. The alpha-1 blockers cause vasodilatation while the beta-1 blockers decrease heart rate and cardiac contractility, all responses which cause a decrease in blood pressure. Conversely, beta-2 blockers reduce flow to muscles and favor bronchial constriction.

While these drugs can be effective in controlling blood pressure, they are often accompanied by a number of deleterious side effects, including impotence. Examples of commonly used antihypertensive drugs which cause impotence include the alpha blockers, beta blockers, and centrally acting anti-adrenergic medications such as methyldopa, clonidine, reserpine, and guanabenz. (Gilman, A., et al., *The Pharmacological Basis of Therapeutics* 177 (1990)). Since hypertension is a common illness of the sexually active population, the risk of impotence is an important consideration when putting these patients on antihypertensive medications. Some patients who experience impotence while taking such medications will independently discontinue them rather than be deprived of their ability to have sex, ignoring the possibility of heart attack and stroke from uncontrolled hypertension. Unfortunately, the value placed on sex outweighs concern about uncontrolled hypertension in these understandably frustrated patients. Furthermore, there is no known cure for impotence of the type lacking a demonstrable organic cause.

It is therefore an object of the present invention to provide a method and composition for treating impotence in patients who have no demonstrable organic cause for the disorder.

It is a further object of the present invention to provide a method and composition for treating patients with impotence caused iatrogenically by medications such as antihypertensives.

SUMMARY OF THE INVENTION

The present invention is a method and compositions for enteral treatment of patients with impotence of no demonstrable organic cause. The method and compositions can also be used to treat impotence caused by antihypertensive medications.

In the preferred embodiment, a drug producing nonselective alpha blockade, such as dibenzyline, in combination with a beta-blocking drug which also possesses vasodilator activity, such as labetolol, celiprolol, and carvedilol, is administered once or twice daily to a patient suffering from impotence. The combination produces a reciprocally balanced autonomic blockade of alpha and beta receptors which restores sexual function.

The method is particularly well suited for patients taking antihypertensive medications since both components have an antihypertensive effect. Another advantage is the infrequency of required dosing, administration being necessary only once or twice a day.

DETAILED DESCRIPTION OF THE INVENTION

The two stages of the male sexual act are erection and ejaculation, both of which are neurally governed. The first stage, erection, has been thought to be mediated by the parasympathetic nervous system whose activity may be inhibited by alpha adrenergic tone. Cholinergic impulses from the spinal cord cause arterial dilatation and venous constriction in the penis. The arterial blood in the erectile tissue of the penis builds up under high pressure due to the venous constriction which blocks the outflow of blood from the penis. The second stage, ejaculation, is thought to be mediated by the sympathetic nervous system. Sensory nerves in the penis respond to sexual stimulation by sending sensory impulses to the spinal cord. After processing these impulses, the spinal cord sends sympathetic impulses to the male reproductive organs. These sympathetic impulses stimulate alpha-1 adrenergic receptors in these reproductive organs, causing them to contract. This contraction results in the filling of the internal urethra with sperm and prostatic fluid. The corresponding pressure increase in the internal urethra stimulates pressure receptors which send impulses to the spinal cord. Cholinergic impulses are then sent from the spinal cord to the penis where the skeletal muscle surrounding the erectile tissue is stimulated to contract, causing ejaculation of the sperm from the internal urethra.

The method and compositions described herein is a system of enteral drug therapy to correct impotence in patients having no demonstrable organic cause for the disorder. The method employs antihypertensive drugs of the same type often used in normotensive states wherein they have little or no effect on blood pressure. Accordingly, the method is basically applicable to normotensive people. However, it is also useful for treating impotence in hypertensive individuals, particularly when the problem may actually have been caused by their prior hypertensive drug regimen.

The method exploits the seemingly paradoxical observations which have established that sexual function can be impaired by either alpha or beta blocking drugs as well as by the selective administration of either alpha or beta agonists. Surprisingly, it has been found that using certain anti-adrenergic, antihypertensive agents to block both the alpha and beta receptors restores or sustains the normal sexual process.

In the preferred embodiment, a drug producing non-selective alpha blockade of both alpha-1 and alpha-2 receptors, such as dibenzyline, is administered once or twice daily in combination with a beta-blocking drug which also possesses vasodilator activity, such as labetolol, celiprolol, or carvedilol, to a patient suffering from impotence. The combination produces a reciprocally balanced autonomic blockade of alpha and beta receptors which restores sexual function.

The method is particularly well suited for patients requiring antihypertensive medications since both components can also have an antihypertensive effect. Another advantage is the infrequency of required dosing, administration being necessary only once or twice daily.

The preferred alpha blocker is dibenzyline, 10 mg administered once or twice daily. Dibenzyline, given by itself, has little beneficial effect on sexual performance, possibly because its use is associated with some fall in blood pressure, venous pooling, and reactive tachycardia from reflex activation of the unblocked beta sympathetic nervous system. In fact, dibenzyline given by itself has been reported to actually cause either impotence or impaired ejaculation in patients. Gilman, A., et al., *The Pharmacological Basis of Therapeutics* 183 (1980).

Alternatively, other non-selective alpha blocking drugs may be substituted: priscoline, 25 to 50 mg once or twice daily, or phentolamine, 50 mg daily. Phentolamine is not preferred since it often causes nausea and vomiting.

The non-selective alpha blockade is administered in combination with a particular type of beta-blocker that also possesses intrinsic vasodilating activity, such as labetalol, celiprolol, or carvedilol. The vasodilator activity of the effective beta blocking agents involves either alpha-1 blockade, beta-2 agonism, calcium channel blockade, or some other type of non-specific vasodilation, or a combination thereof. Effectiveness in combination with dibenzyline has been shown for labetolol, 200 to 400 mg, administered twice to three times daily; celiprolol, 200 mg, administered twice daily; and carvedilol, 25 mg, administered once or twice daily. Preferred dosage ranges are 25 mg once daily for carvedilol, and 200 mg twice daily for labetolol and celiprolol. Use of older types of beta blockers such as non-selective (e.g. propranolol) or cardioselective (e.g., atenolol or metoprolol) beta blockers, alone or in combination with the alpha blockade induced by the first drug, produce either no correction or a worsening of impotence.

The drugs are preferably administered enterally, most preferably in combination in a pharmaceutically acceptable vehicle, such as a tablet. Other methods and forms of administration will be obvious to those skilled in the art. The effective dosages can be determined by one of ordinary skill in the art, based on the dosages approved for other uses combined with empirical observations.

In another alternative embodiment, the present method and compositions could be used to restore sexual function in females and to treat sexual dysfunction associated with a range of disturbances of the cardiovascular system, including the aging process. It can also be used to design improved antihypertensive drug regimens that maintain sexual function and avoid drug-induced impotence.

The present invention will be further understood by reference to the following non-limiting examples.

The method and compositions emerged from the critical serial testing of prototypical anti-adrenergic, antihypertensive agents over an extended period of time. The agents were first administered and evaluated when given alone and then in various possible combinations to search for a means for allowing or enhancing potency (measured by erection) or the time of a sexual encounter.

Potency was graded on a scale of 0 to 4, with a 3 or 4 grade requiring capacity for penetration and completion of the sexual act. The strategy employed involved a modification of the well-known "N of 1" design, described by Guyatt, et al., *N. E. J. Med.* 314, 889–892 (1986), the teachings of which are incorporated herein. In this strategy, any positive result is systematically verified by repeated comparison with what happens in the control states, as well as when an alternative treatment is applied with a known effect or lack of one.

All agents tested using this strategy showed extremely high internal consistency as to either a positive effect or lack thereof. Routinely, the two agents were given once or twice daily, at least two hours before an anticipated sexual encounter. All drug types were evaluated for their short term effects, i.e., from 2 to 24 hours after oral administration. However, such acutely positive actions, when demonstrable, did not disappear when longer term usage was evaluated for up to three to six months.

EXAMPLE 1

Administration of anti-adrenergic or other hypertensive agents alone.

Typical beta-blockers were administered to patients in full daily dosages for a week or longer. Propranolol, 40 mg, was administered t.i.d.; atenolol, 25 or 50 mg, was administered once daily; metoprolol, 100 mg, was administered twice daily; pindolol, 10 mg, was administered once daily.

No positive effects were observed.

Similar uniformly negative results were obtained using other types of agents administered alone, including the alpha-1 blocker, prazosin, in doses up to 5 mg three times daily, and the calcium antagonists, verapamil, 250 mg, twice daily; diltiazem, 90 mg, three times daily; and nifedipine, 20 mg, three times daily.

Non-selective alpha blockade administered alone was similarly evaluated, using phentolamine, 50 mg, once daily; priscoline, 25 to 50 mg, twice daily; and dibenzyline, 10 mg, once or twice daily. Phentolamine can produce partially positive results, but its usage in the two individuals studied consistently caused marked nausea and vomiting within two hours of taking the medications, well known side effects of the drug. Priscoline, 50 mg, twice daily, produced only questionable benefit at best (score=1), as did dibenzyline. This was also true for the alpha-2 blocker yohimbine, 30 mg, once daily. Moreover, these agents, when administered alone, all tended to cause reactive tachycardia, nasal stuffiness, and, in the case of yohimbine, evidence of central nervous stimulation of sympathetic outflow.

EXAMPLE 2

Administration of Beta-blocker having vasodilating activity.

Certain beta-blockers also have vasodilating activity, resulting from alpha-1 blockade, from beta-2 agonism arising from a degree of calcium entry antagonism or from non-specific vasodilation. These drugs were tested when administered alone. Labetolol, up to 400 mg, was administered three times daily; celiprolol, 200 mg, was administered once or twice daily; and carvedilol, 25 mg, administered once or twice daily, were tested.

All three agents, when administered alone, gave a weakly positive benefit to sexual performance. (score =1 or 2) These responses are different than the negative effects observed with beta blockers that do not possess vasodilator activity.

EXAMPLE 3

Administration of Dibenzyline in Combination with the Vasodilatory Beta Blockers Labetalol, Celiprolol and Carvedilol.

The vasodilatory beta-blockers labetalol, celiprolol, and carvedilol, were retested in combination with a background of maintained non-selective alpha-1 and alpha-2 blockade, produced by administration of dibenzyline, 10 mg, once or twice daily. As demonstrated by Example 1, dibenzyline alone produces little or no beneficial effects on potency and it can impair ejaculation. The lack of benefit may be related to side effects, usually minor in degree, that involve postural hypotension and tachycardia from reactive activation of the beta adrenergic system. Dibenzyline is normally used in much larger dosages to control the blood pressure of a pheochromocytoma (adrenaline or noradrenaline secreting tumors) and to promote urine flow in benign prostatic hypertrophy, usually in dosages of 10 to 40 mg daily. In the present study, the drug caused no untoward side effects and no impairment of vigor or exercise capacity at the dosages used.

Priscoline, 25 or 50 mg, administered once or twice daily, was also effective, although slightly less so than the dibenzyline. Prazosin was not effective.

EXAMPLE 4

Administration of Dibenzyline in Combination with Beta Blockers propranolol, metoprolol, atenolol, and pindolol.

The older typical beta blockers, propranolol, metoprolol, atenolol, and pindolol, were combined with dibenzyline and tested for their effect on impotence. These compounds do not have vasodilator activity.

These combinations produced either no benefit or worsening of impotence, reemphasizing that only beta blockers which also have vasodilator activity (attributable to alpha-1 blockade, beta-2 agonism, calcium channel blockade, or non-specific vasodilation) can work in combination with the non-selective alpha-1 and alpha-2 blockade to enable or enhance sexual responsiveness.

Modifications and variations of the present invention, a method and compositions for treating impotence, will be obvious to those skilled in the art from the foregoing detailed description, and are intended to come within the scope of the appended claims.

I claim:

1. A method for treating impotence in patients comprising enterally administering to a male patient suffering from impotence an effective amount of the combination of a non-selective alpha-1 and alpha-2 adrenergic blocking drug and a beta adrenergic blocking drug having vasodilator activity.

2. The method of claim 1 wherein the drugs are administered orally at least once a day to the patient.

3. The method of claim 1 wherein the alpha adrenergic blocking drug is selected from the group consisting of dibenzyline, priscoline, and phentolamine.

4. The method of claim 1 wherein the beta adrenergic blocking drug is selected from the group consisting of labetalol, celiprolol, and carvedilol.

5. A composition for treating impotence in male patients comprising an effective amount of the combination of a non-selective alpha adrenergic blocking drug and a beta adrenergic blocking drug having vasodilator activity in a pharmaceutically acceptable vehicle for enteral administration to a patient.

6. The composition of claim 5 wherein the alpha adrenergic blocking drug is selected from the group consisting of dibenzyline, priscoline, and phentolamine.

7. The composition of claim 6 wherein the composition contains between 5 and 50 mg of dibenzyline.

8. The composition of claim 6 wherein the composition contains between 25 and 200 mg priscoline.

9. The composition of claim 5 wherein the beta adrenergic blocking drug is selected from the group consisting of labetalol, celiprolol, and carvedilol.

10. The composition of claim 9 wherein the composition contains between 10 and 50 mg carvedilol.

11. The composition of claim 9 wherein the composition contains between 200 and 500 mg of a compound selected from the group consisting of labetolol and celiprolol.

* * * * *